United States Patent [19]

Sutherland

[11] Patent Number: 4,753,229

[45] Date of Patent: Jun. 28, 1988

[54] ANKLE BRACE

[76] Inventor: Tom Sutherland, 1225 Westfield Ave., Reno, Nev. 89509

[21] Appl. No.: 927,888

[22] Filed: Nov. 6, 1986

[51] Int. Cl.⁴ .......................... A61F 5/37; A61F 5/01; A61F 13/06
[52] U.S. Cl. ..................... 128/80 H; 128/166
[58] Field of Search ............................. 128/80 H, 166

[56] References Cited

U.S. PATENT DOCUMENTS

| | | | |
|---|---|---|---|
| 3,050,053 | 8/1962 | Peckham | 128/80 H |
| 3,073,305 | 1/1963 | Biggs, Jr. et al. | 128/80 H |
| 3,312,219 | 4/1967 | Peckham | 128/166 |
| 3,383,708 | 5/1968 | Pappas | 2/22 |
| 3,506,000 | 4/1970 | Baker | 128/166 |
| 3,699,959 | 10/1972 | Garrahan et al. | 128/166 |
| 3,777,751 | 12/1973 | Wise | 128/166 |
| 4,085,746 | 4/1978 | Castiglia | 128/166 |
| 4,345,590 | 8/1982 | Nakajima | 128/166 |
| 4,367,733 | 1/1983 | Stromgren | 128/166 |
| 4,392,487 | 7/1983 | Selner et al. | 128/80 H |
| 4,409,976 | 10/1983 | Fence | 128/80 H |
| 4,489,719 | 12/1984 | Lapenskie | 128/80 H |
| 4,547,981 | 10/1985 | Thais et al. | 128/80 H |
| 4,556,054 | 12/1985 | Paulseth | 128/166 |
| 4,621,648 | 11/1986 | Ivany | 128/80 H |
| 4,646,726 | 3/1987 | Westin et al. | 128/80 H |

FOREIGN PATENT DOCUMENTS 183418 4/1907 Fed. Rep. of Germany ...... 128/166
511968 10/1930 Fed. Rep. of Germany ... 128/80 H Primary Examiner—Edgar S. Burr
Assistant Examiner—Tonya Lamb
Attorney, Agent, or Firm—Townsend and Townsend

[57] ABSTRACT

A reusable ankle brace for preventing lateral ankle sprains. The brace is constructed from an ankle cuff and a foot piece, with three straps emanating from anchor points on the foot piece for engagement with the ankle cuff. A first strap extends across from the heel end of the lateral side of the foot and across the front of the ankle, and is secured to the ankle cuff at the anteriomedial aspect. A second strap extends from the outside arch side portion of the foot vertically upward to a lateral side portion of the ankle cuff. A third strap is attached from the front end of the outside of the foot around the rear of the ankle and attaches on the posteriormedial aspect of the ankle cuff. The straps may be removably anchored on the ankle strap with hook and loop fasteners threaded through rings secured to the ankle cuff or removably anchored to the exterior counter portion of a shoe. The foot piece of one embodiment comprises a planar sheet to which the straps are anchored, with the sheet wrapped around the instep of the wearer's foot. In a second embodiment, the foot piece is an orthotic such as an arch support. In the third embodiment, the straps are removably secured to a shoe counter and are fixed to the ankle cuff.

8 Claims, 1 Drawing Sheet

U.S. Patent   Jun. 28, 1988   4,753,229
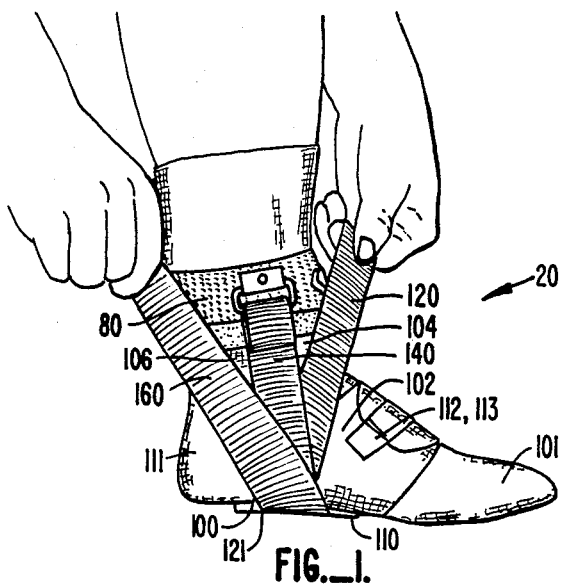
FIG._1.
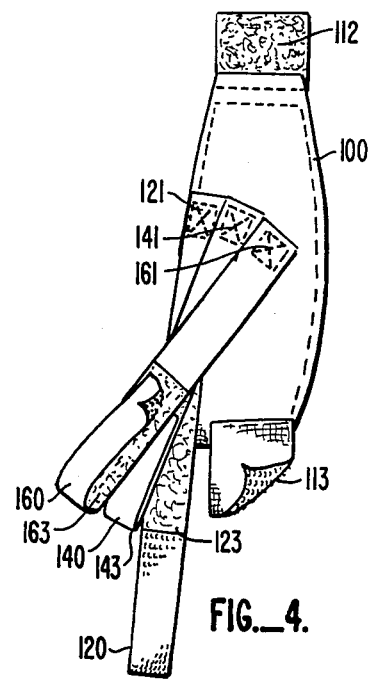
FIG._4.
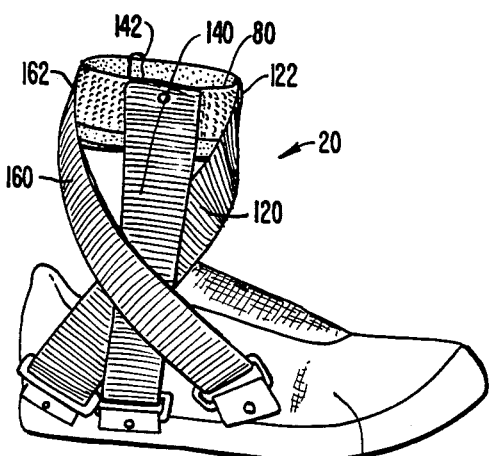
FIG._2.
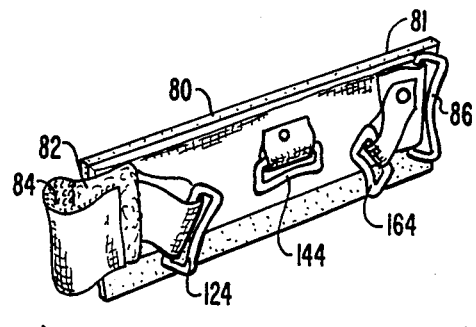
FIG._5.
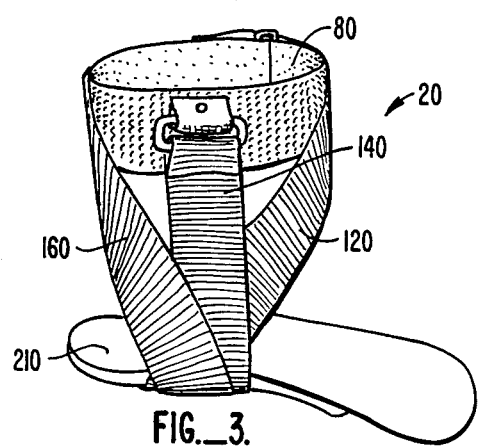
FIG._3.

ANKLE BRACE

BACKGROUND OF THE INVENTION

The present invention relates to an ankle brace for the prevention of lateral ankle sprains.

Many athletes are injured for days and weeks by ankle sprains. Some individuals are also susceptible to ankle sprains, especially during strenuous activities such as running. Many braces have been proposed to prevent ankle sprains, but none have proven satisfactory.

There are two types of ankle sprains—medial or inside ankle sprains, and lateral or outside ankle sprains. Approximately 90% of all ankle sprains are lateral sprains. Lateral sprains are a result of inversion movement of the foot with such force that the anterior talofibular ligament and/or the calcaneofibular ligament are sprained.

The most effective means of ankle support and the most widely used method in athletics, is the wrapping of the ankle with supportive adhesive tape strapping. Wrapping of the ankles is routinely performed in athletics by coaches, trainers, and team physicians. Such a procedure is expensive in that the tape itself is expensive and not reusable, and because of the time it takes the trained personnel to apply the strapping.

A number of reusable ankle supports comprising elasticized members or pluralities of straps have been proposed, but have been found cumbersome, or structurally unacceptable for preventing lateral sprains.

SUMMARY OF THE INVENTION

A reusable ankle brace is disclosed which comprises a foot piece, an ankle cuff and three straps.

The foot piece is placed on or under the foot with the three straps attached to its lateral side. One embodiment of the foot piece extends medially and laterally to encircle the foot. It is removably secured and adjustable. The foot piece can alternatively take the form of an insole or an orthotic device with the straps attached thereto. The straps can also be removably attached to the exterior lateral side of a shoe counter.

The ankle cuff of one embodiment is removable, adjustable and encircles the ankle. The three straps extend from the foot piece to the ankle cuff. A first strap is secured at a first anchor point towards the heel end of the foot piece along the lateral side, wraps around the front of the ankle and is secured to the anteriomedial aspect of the ankle cuff. A second strap is secured at a second anchor point at mid-arch position along the lateral edge of the foot piece and extends generally vertically to be secured to the lateral side of the ankle. A third strap is secured at a third anchor point towards the front of the lateral side of the foot piece, wraps around the back of the ankle and is secured to the posteriormedial aspect of the ankle cuff. The straps are removable at either their connections to the ankle cuff, or at their connection to the foot piece, or at both ends.

The ankle brace of the present invention is designed to prevent lateral ankle sprains. It reinforces the anterior talofibular ligament and the calcaneofibular ligament. The brace limits inversion, which is the movement that causes lateral sprains. The ankle brace supplants the supportive tape wrapping procedure and is only applied to the lateral side of the ankle, thus minimally encumbering the wearer and providing freedom of movement in any direction other than the lateral direction.

Motion of the foot and ankle is not hindered with the exception of inversion. Normal subtalor joint motion is unrestricted, as is dorsiflexion and plantarflexion. This degree of freedom of movement provides the wearer with a greater range of motion for better performance than is possible with other more restrictive support measures.

The ankle brace is constructed so as to be flexible and soft, but not elastic. The portions contracting the skin of the wearer should be coated with a rubber-like foam to prevent slippage between the skin and the brace. In the preferred embodiments, the ankle brace is constructed from machine washable materials for easy maintenance and cleaning. The construction of the ankle brace is relatively uncomplicated, resulting in reduced costs of manufacturing and reduced costs to the consumer.

The simplicity of design of the ankle brace permits it to be properly applied without difficulty, with the application of the brace to each foot taking only a few seconds. The ankle brace is reusable until the materials of construction are worn or frayed.

Other features and advantages of the invention will appear from the following description in which the preferred embodiments are discussed in detail in conjunction with the accompanying drawings.

BRIEF DESCRIPTION OF THE DRAWINGS

FIG. 1 illustrates one form of the ankle brace as it is worn on the foot;

FIG. 2 is an embodiment of the ankle brace incorporated into a shoe;

FIG. 3 is an embodiment of the ankle brace wherein the straps are secured to an arch support;

FIG. 4 is an illustration of the foot piece and strap components of the ankle brace; and FIG. 5 is a detailed description of the ankle cuff.

DETAILED DESCRIPTION OF THE INVENTION

In the illustration of FIG. 1, an ankle brace 20 is shown to include a foot piece 100 which is wrapped around the arch 110 of foot 101. In this embodiment, foot piece 100 encircles the arch 110 of the foot about the instep and is secured at its end on the top of the foot by a strip 112 of loop closure material secured to the top surface of one end of foot piece 100 to engage a strip 113 of hook closure material secured to the opposite end.

A first strap 120 emanates from a position 121 on the foot piece 100 towards the heel 111 from the lateral (outside) side 102 of the foot 101, and extends across the front area 104 of the ankle 106 to be secured at the anteriomedial aspect of the ankle cuff 80. A second strap 140 is secured near the arch portion of foot piece 100, in front of the position where first strap 120 is secured, and extends generally upward to be secured at the lateral aspect of ankle cuff 80. A third strap 160 is secured further forward along foot piece 100 than the second strap 140, and extends towards the heel and around the rear of the ankle to be secured on the posteriormedial aspect of the ankle cuff 80.

The maximum benefit to the wearer, the straps should be secured in the order described above, with the foot in an everted position, and the straps applied with tension. The ankle cuff 80 is a strap of cotton webbing. A suitable webbing is available from Elizabeth Webbing Mills. It is untreated, 3/64" thick, military spec. #W-

530F. It is secured around the ankle by a strip of loop closure material 82 secured near one end of ankle cuff 80, and an extending strip of hook closure material 84 fastened to the same end. A ring 86 is secured to the opposite end of ankle cuff 80. Hook strip 84 is threaded through ring 86 and folded back upon loop strip 82 to tighten and secure ankle cuff 80 around the wearer's ankle.

The additional embodiments of the invention provide different foot pieces to which the same arrangement of straps is secured. FIG. 2 illustrates the straps 120, 140 and 160 removably secured to the exterior counter portion of a shoe 200, which acts as the foot piece. The ends of the straps are removably secured along the lateral side of the outside surface of the shoe's counter, thus eliminating the added thickness of the straps inside the shoe. The upper ends of the straps 122, 142 and 162 may either be fixedly or removably attached to ankle cuff 80. With straps 120, 140 and 160 removably securable to the exterior counter of the shoe, the shoes may be worn either with or without the benefit of the ankle support.

FIG. 3 illustrates the straps 120, 140 and 160 emanating from the lateral side of an orthotic device such as an arch support 210. The present invention can be combined with another orthotic device to provide multiple benefits to the wearer, without the necessity of wearing multiple devices.

The basic elements of the ankle brace are shown in FIGS. 4 and 5. Sole piece 100 is an instep cuff which, when unfolded, is planar as shown in FIG. 4. A suitable material for the foot piece is an 18 ounce vinyl coated fabric sold under the name Cooleys-TXN. The foot piece is also provided with a soft rubber-like cushion on the surface which contacts the skin. A suitable material is an insole material made by Spenco. The three straps 120, 140 and 160 are secured to the undersurface of foot piece 100 from their respective anchor positions 121, 141 and 161. The free ends of the straps 120, 140, 160 terminate in sections 123, 143 and 163 respectively, of hook and loop fastener tape for threading through the rings 124, 144 and 164 attached to ankle cuff 80 (FIG. 5). Ankle cuff 80 is provided with a soft rubber cushion 81 on the surface which contacts the skin for additional comfort and to prevent slippage. A suitable material is an insole material made by Spenco.

The various embodiments of the present invention provide for customized lateral support of the wearer's foot to prevent or rehabilitate lateral ankle sprains. The invention is adaptable to any size foot. The individual wearer may decide on the degree of tightness and tautness with which the ankle brace is applied. Adjustment is very simple, and the application does not require the assistance of trained personnel.

The ankle brace of the present invention is quite durable and reusable, yet easy and inexpensive to manufacture. The components of the foot piece and ankle cuff are adjustable to fit a range of sizes, thus minimizing the number of patterns required to manufacture the ankle braces. For instance, the foot piece shown in FIGS. 1 and 4 may be adjusted by securing the foot piece around the instep such that the straps 120, 140 and 160 are either shorter or longer depending on how much of the length of the straps is wrapped underneath the foot and foot piece.

The foot piece of the ankle brace can be chosen to suit the particular activity. For instance, for sports in which no shoes or very lightweight footwear are worn, the bare foot piece of FIGS. 1 and 4 might be used. For athletes with arch problems, the arch support orthotic combined with the ankle brace, worn within the shoe, would be best. For athletic events in which special shoes are worn, such as wrestling, basketball, football and baseball, the embodiment in which the straps are removably secured directly to the counter of the shoe would be most suitable.

Other alternative embodiments which achieve equivalent features of the present invention would be apparent to those skilled in the art. For instance, once the first, second and third straps had been properly adjusted by the wearer and secured to the ankle cuff, their positions along the ankle cuff could be made permanent. This would render the ankle cuff and the straps into a single element. The wearer would then only need to wrap the ankle cuff to apply the brace on subsequent wearings of the ankle brace. From the above description, it is intended that this disclosure be taken in an exemplary sense, and the scope of protection afforded be determined by the appended claims.

What is claimed is:

1. A reusable ankle brace for supporting and reinforcing the anterior talofibular ligament and the calcaneofibular ligament, comprising:

a foot piece, at least a portion of said foot piece worn around the foot;

an ankle cuff, said ankle cuff removably wrapped around the ankle and secured by reusable securing means;

a first strap, having a first end secured to and extending from said foot piece from a first rearward anchor point located along a lateral edge of said foot piece, said first strap extending across the front of the ankle and secured at a second end to said ankle cuff to a second anchor point on an anteriomedial portion of said ankle cuff;

a second strap, having a third end secured to and extending from said foot piece from a third medial anchor point located along said lateral edge of said foot piece, said second strap extending generally vertically upward along the lateral side of the wearer's foot and secured at a fourth end to a fourth anchor point located at a lateral portion of said ankle cuff; and a third strap, having a fifth end secured to and extending from said foot piece from a fifth forward anchor point located along said lateral edge of said foot piece, said third strap extending across the back of the ankle and secured at a sixth end to a sixth anchor point located at a posteriormedial portion of said ankle cuff, said straps being permanently secured to one of said foot piece or said ankle cuff and being removably secured to the other of said foot piece or said ankle cuff by reusable securing means, said first, second and third straps laterally supporting the anterior talofibular ligament and the calcaneofibular ligament.

2. The ankle brace of claim 1, wherein said foot piece comprises a shoe counter, and said first, third, and fifth anchor points are located on an exterior lateral counter surface of the shoe.

3. The ankle brace of claim 2, wherein said first second and third straps are removably secured, respectively at said first, third and fifth anohor points.

4. The ankle brace of claim 1, wherein said foot piece comprises a generally planar sheet which wraps about the instep region of the wearer's foot and will fit inside of a conventional shoe.

5. The ankle brace of claim 1, wherein said second, fourth and sixth ends of said first, second and third straps further comprise sections of hook and loop fastener tape, and said ankle cuff further comprises first, second and third rings, said sections of hook and loop fastener tape of said first, second and third straps threaded respectively through said first, second and third rings such that the hook section of said fastener tape engages the loop section of said fastener tape.

6. The ankle brace of claim 1, wherein said foot piece comprises an orthotic.

7. The ankle brace of claim 6, wherein said orthotic comprises an arch support.

8. The ankle brace of claim 1, wherein said ankle cuff further comprises a first end having a section of hook and loop fastener tape and a second end having a ring through which said section of hook and loop fastener tape may be threaded such that the hook section of said fastener tape engages the loop section of said fastener tape.

* * * * *